United States Patent [19]
Geddes et al.

[11] Patent Number: 6,096,347
[45] Date of Patent: Aug. 1, 2000

[54] MYOCARDIAL GRAFT CONSTRUCTS

[75] Inventors: Leslie A. Geddes; Stephen F. Badylak, both of West Lafayette; Robert G. Matheny, Carmel; William E. Schoenlein, Lafayette; Fred J. Obermiller, West Lafayette; William J. Havel, Lafayette, all of Ind.

[73] Assignee: Purdue Research Foundation, West Lafayette, Ind.

[21] Appl. No.: 09/297,621

[22] PCT Filed: Nov. 4, 1997

[86] PCT No.: PCT/US97/20240

§ 371 Date: May 4, 1999

§ 102(e) Date: May 4, 1999

[87] PCT Pub. No.: WO98/19719

PCT Pub. Date: May 14, 1998

Related U.S. Application Data

[60] Provisional application No. 60/030,211, Nov. 5, 1996.
[51] Int. Cl.⁷ ...................................................... A61K 35/38
[52] U.S. Cl. ................................ 424/551; 623/2; 623/11; 623/14
[58] Field of Search ................................ 424/551; 623/2, 623/11, 14

[56] References Cited

U.S. PATENT DOCUMENTS 5,480,424  1/1996  Cox .

FOREIGN PATENT DOCUMENTS

WO96/31157  10/1996  WIPO .

OTHER PUBLICATIONS

"Fascia lata replacement of aortic valves," *The Journal of Thoracic And Cardiovascular Surgery*, Ake Senning, vol. 54, No. 4, Oct. 1967, pp. 465–470.

"Mitral and aortic valve replacement with fascia lata on a frame," *The Journal of Thoracic And Cardiovascular Surgery*, W. Sterling Edwards, et al., vol. 58, No. 6, Dec. 1969, pp. 854–858.

*Primary Examiner*—Jean C. Witz
*Attorney, Agent, or Firm*—Barnes & Thornburg

[57] ABSTRACT

The use of submucosal tissue of a warm blooded vertebrate to manufacture a tissue graft composition that induces the formation of endogenous cardiac tissues in vivo upon contact of the cardiac tissues with the manufactured composition.

27 Claims, 6 Drawing Sheets

MYOCARDIAL GRAFT CONSTRUCTS

CROSS-REFERENCES TO RELATED APPLICATIONS

This application is a U. S. national application of international application Ser. No. PCT/US97/20240 filed Nov. 4, 1997, which claims priority to U.S. provisional application Ser. No. 60/030,211 filed Nov. 5, 1996.

FIELD OF THE INVENTION

The present invention relates to a tissue graft composition and methods for its preparation and use. More particularly, the present invention is directed to non-immunogenic submucosal tissue graft compositions prepared from warm-blooded vertebrates and the use of those compositions to promote growth of endogenous cardiac tissues.

BACKGROUND AND SUMMARY OF THE INVENTION

It is known that compositions comprising the tunica submucosa of the intestine of warm-blooded vertebrates can be used as tissue graft materials. See U.S. Pat. Nos. 4,902,508 and 5,281,422. The tissue graft compositions described in those patents are characterized by excellent mechanical properties, including a high burst pressure, and an effective porosity index which allows such compositions to be used beneficially for vascular graft and connective tissue graft constructs. When used in such applications the graft constructs appear not only to serve as a matrix for the regrowth of the tissues replaced by the graft constructs, but also promote or induce such regrowth of endogenous tissue. Common events to this remodeling process include: widespread and very rapid neovascularization, proliferation of granulation mesenchymal cells, biodegradation/resorption of implanted intestinal submucosal tissue material, and absence of immune rejection.

It is also known that intestinal submucosa can be fluidized by comminuting and/or enzymatic digestion, without loss of its apparent biotropic properties, for use in less invasive methods of administration (e.g., by injection or topical application) to host tissues in need of repair. See U.S. Pat. No. 5,275,826.

Surprisingly, it has been found that submucosal tissue is also capable of promoting endogenous regrowth and healing of damaged or diseased cardiac tissues, including the endocardium, pericardium, and myocardium. Myocardial tissue comprises the middle muscular tissue of the heart wall. Cardiac muscle tissue differs from smooth and skeletal muscle in that the nuclei are centrally located, the cells form a syncytium, and the cells exhibit the property of spontaneous contractibility or "automaticity."

In accordance with the present invention submucosal tissue of a warm blooded vertebrate is used for the preparation of a graft construct that promotes endogenous regrowth and healing of damaged or diseased cardiac tissues upon contact of said damaged or diseased tissues with the composition.

The present submucosal tissue graft compositions can be implanted or injected into a vertebrate host to induce the repair or replacement of damaged or defective heart tissues. In one embodiment damaged or diseased myocardial tissues are contacted in vivo with a composition comprising intestinal tunica submucosa of a warm blooded vertebrate to enhance the formation of endogenous tissues having spontaneous contractile properties.

DETAILED DESCRIPTION OF THE INVENTION

Figure 1:
FIG. 1 illustrates myographic data for remodeled canine ventricular myocardium. Spontaneous contractions (1, 2 and 3) and an evoked contraction (50 ms, 160 mA) were observed in the remodeled tissue from the MV2 dog.

There is provided in accordance with this invention a method and composition for promoting the repair of damaged or diseased heart tissues. Generally the method comprises the step of contacting target cells in vivo with a vertebrate derived collagenous matrix. The collagenous matrix compositions of the present invention can be injected or implanted into a host to induce the formation of endogenous heart tissues including the formation of spontaneously contractile myocardial tissues.

The collagenous matrix for use in preparing the compositions of the present invention can be selected from a variety of commercially available collagen matrices or can be prepared from a wide variety of natural sources of collagen. In preferred embodiments the collagenous matrix for use in accordance with the present invention comprises highly conserved collagens, glycoproteins, proteoglycans, and glycosaminoglycans in their natural configuration and natural concentration. Most preferably the collagenous matrix comprises submucosa-derived tissue of a warm-blooded vertebrate. Submucosal tissue can be obtained from various vertebrate organ sources (such as intestinal tissue) harvested from animals raised for meat production, including, for example, pigs, cattle and sheep or other warm-blooded vertebrates.

The submucosal tissue used in accordance with the present invention is preferably derived from the intestines, more preferably the small intestine, of a warm blooded vertebrate. Preferred intestinal submucosal tissue typically comprises the tunica submucosa delaminated from both the tunica muscularis and at least the luminal portions of the tunica mucosa. In one preferred embodiment of this invention the submucosal tissue comprises the tunica submucosa and basilar portions of the tunica mucosa including the lamina muscularis mucosa and the stratum compactum. The preparation of submucosal tissue for use in accordance with this invention is described in U.S. Pat. No. 4,902,508, the disclosure of which is expressly incorporated herein by reference. A segment of vertebrate intestine, preferably harvested from porcine, ovine or bovine species, is first subjected to gentle abrasion using a longitudinal wiping motion to remove both the outer layers, identified as the tunica serosa and the tunica muscularis, and the innermost layer, i.e., the luminal portions of the tunica mucosa. The submucosal tissue is rinsed with water or saline, optionally sterilized, and can be stored in a hydrated or dehydrated state. Delamination of the tunica submucosa from both the tunica muscularis and at least the luminal portions of the tunica mucosa and rinsing of the submucosa provides an acellular matrix designated as submucosal tissue. The use and manipulation of such material for the formation of ligament and tendon grafts and the use more generally of such submucosal tissue constructs for inducing growth of endogenous connective tissues is described and claimed in U.S. Pat. No. 5,281,422 issued Jan. 25, 1994, the disclosure of which is expressly incorporated herein by reference.

It is also known that fluidized forms of submucosal tissue can be prepared without loss of the submucosal tissue's ability to induce the growth of endogenous tissues. Fluidized submucosa compositions comprise comminuted submucosa or enzymatically treated submucosa, and in one embodiment the submucosal tissue is comminuted and enzymatically treated to form a substantially uniform or homogenous solution. In one embodiment, the submucosa is treated with a protease, such as trypsin or pepsin, or other appropriate enzymes for a period of time sufficient to solubilize said tissue and form a substantially homogeneous solution. The preparation of fluidized forms of intestinal submucosa is described in U.S. Pat. No. 5,275,826, the disclosure of which is expressly incorporated herein by reference.

The present invention also contemplates the use of powder forms of submucosal tissues. In one embodiment a powder form of submucosal tissue is prepared by pulverizing intestinal submucosa tissue under liquid nitrogen to produce particles ranging in size from 0.01 to 1 mm in their largest dimension. The particulate composition is then lyophilized overnight, pulverized again and optionally sterilized to form a substantially anhydrous particulate composite. Alternatively, a powder form of submucosal tissue can be formed from fluidized submucosal tissue by drying the suspensions or solutions of comminuted submucosal tissue. Both solid and fluidized forms of intestinal submucosa have been found, upon implantation or injection to induce endogenous remodeling processes including rapid neovascularization, proliferation of granulation mesenchymal cells, resorption of the implanted submucosa tissue and absence of immune rejection. In vivo, implanted submucosa tissue has been found effective to induce the proliferation and growth of cells/tissues with which it is in contact or which it replaces.

Because of the unique characteristics and highly specialized nature of myocardial tissue and the knowledge that damaged myocardial tissue heals by scar (non-contractile) tissue formation in mammals, it was not anticipated that submucosal tissue could induce the formation of endogenous myocardial tissues. Surprisingly, the submucosa graft constructs of the present invention promote endogenous regrowth and healing of damaged or diseased cardiac tissues (including the endocardium, pericardium, and myocardium) when the graft constructs are placed in contact with the endogenous cardiac tissues and exposed to the same natural microenvironment as the endogenous cardiac tissues.

Submucosal tissues used in accordance with the present invention lend themselves to a wide variety of surgical applications relating to the repair or replacement of damaged heart tissues, including, for example the repair or replacement of myocardial, endocardial and pericardial tissues. Submucosal tissue grafts are used to induce the formation of endogenous myocardial tissue at a desired site in the heart of a warm blooded vertebrate. The submucosal tissue compositions can be administered to the host in either solid sheet, strip or loop form, by surgical implantation, or in fluidized form, by injection. Solid sheet and strip forms of submucosal tissue have been previously described in U.S. application Ser. No. 08/418,515 and PCT application Ser. No. PCT/US96/04721 the disclosures of which are expressly incorporated herein by reference. The loop form of submucosal tissue comprises a continuous strip of submucosal tissue formed into a multilaminate structure by wrapping the strip onto itself and around at least one axis. Typically the ends of the strip of submucosal tissue forming the loop are immobilized by suturing, gluing, stapling, compressing or utilizing other tissue immobilizing techniques known to those skilled in the art to fix the ends to the remaining graft construct.

One embodiment of the present invention comprises a method for enhancing the formation of spontaneously contractile myocardial tissues. The method comprises contacting heart myocardial tissues in vivo with a composition comprising intestinal submucosal tissue in an amount effective to promote endogenous cardiac tissue growth at the site the composition is administered.

In accordance with one embodiment of the present invention the ability of submucosal tissue to induce the formation of excitation-propagating myocardial tissue is utilized to create an A-V bridge to propagate excitation from the atria to the ventricles in a subject having A-V block. In the United States about 100 thousand cardiac pacemakers are implanted annually. A large majority of these are used to pace the ventricles because the A-V conductive system has been blocked.

Heart block is a disorder of the heart beat that leads to episodes of dizziness or fainting. Heart block is caused by an interruption to the passage of impulses through the specialized conducting system of the heart. Consequently, although the atria beat normally, the ventricles lag behind or contract less often than the atria. In complete heart block the atria and ventricles beat independently; thus while the rate of atrial contractions varies according to the patients activity, the ventricles contract at a fairly constant rate of about 40 beats per minute. In a large percentage of these patients the natural pacemaker (S-A node) and the atria function normally. In these patients submucosal tissue can be implanted into the atrial and ventricular myocardium to remodel into myocardial tissue capable of conducting excitation from the S-A node. Thus, the atrial excitation will be propagated along the submucosal remodeled A-V bridge and the atria will drive the ventricles, thereby eliminating the need for an implanted cardiac pacemaker in patients having a normally function S-A node and atria but suffering from A-V block.

The surgical procedure of implanting the submucosal tissue into the atrial and ventricular myocardium may be performed with the aid of a laparoscope, thereby requiring minimal invasive surgery. The implanted submucosal tissue remodels to atrial and ventricular myocardium capable of conducting excitation from the S-A node to the ventricles. Complete remodeling of the implanted submucosal tissue takes approximately four to eight weeks, during which time a temporary external pacemaker may be used if needed. Accordingly, the use of a submucosal tissue implant will allow the ventricles to be driven by the atria such that the rate of contraction will automatically increase with exercise. Furthermore, no implantable pacemaker is needed and the repair of the A-V bridge should last the entire life of the patient.

In another embodiment fluidized submucosal tissue can be injected into or adjacent to a site in need of endogenous cardiac tissue growth to induce the formation of cardiac tissues such as the myocardium, pericardium and endocardium. For example, submucosal tissue can be injected between the pericardium and the myocardium in an amount effective to induce repair of the damaged or diseased tissue. Alternatively the fluidized submucosal tissue can be injected directly into the damaged or diseased heart tissue in need of repair.

In an alternative embodiment damaged or diseased portions of the heart can be repaired by surgically replacing the affected tissue with a patch of submucosal tissue in solid sheet, strip or loop form. Consistent with the use of submucosal tissue as a patch graft material for replacement of damaged or diseased myocardial tissues, preferred vertebrate intestinal submucosa tissue possesses mechanical properties highly desirable for such tissue graft materials, including low porosity index, a high burst pressure, and a stratum compactum surface with low thrombogenicity.

The submucosa grafts formed and used in accordance with this invention, upon implantation, serve as a rapidly vascularized matrix for support and growth of new endogenous cardiac tissue. The graft material is remodeled (resorbed and replaced with autogenous differentiated tissue) and assumes the characterizing features of the heart tissue with which it is associated at the site of implantation. Indeed, where a single graft "sees" multiple microenvironments as implanted, it is differentially remodeled along its length and thickness. Thus, for example, when used in myocardial tissue replacement studies the graft appears to develop endocardial tissue as well as myocardial tissues.

For myocardial replacement applications submucosal tissue graft constructs are typically "conditioned" to alter the viscoelastic properties of the submucosal tissue. Submucosal tissue is conditioned by stretching, chemically treating, enzymatically treating or exposing the tissue to other environmental factors. The conditioning of submucosal tissue is described in U.S. Pat. No. 5,275,826, the disclosure of which is expressly incorporated herein by reference. In accordance with one embodiment vertebrate derived submucosal tissues are conditioned to a strain of no more than about 20%.

In one embodiment the submucosal tissue is conditioned by stretching the graft material longitudinally to a length longer than the length of the submucosal tissue from which the graft construct was formed. One method of "conditioning" the tissue by stretching involves application of a given load to the submucosa for three to five cycles. Each cycle consists of applying a load to the graft material for five seconds, followed by a ten second relaxation phase. Three to five cycles produces a stretch-conditioned graft material. The graft material does not immediately return to its original size; it remains in a "stretched" dimension. For example, submucosal tissue can be conditioned by suspending a weight from the tissue, for a period of time sufficient to allow about 10 to 20% or more elongation of the tissue segment. Optionally, the graft material can be preconditioned by stretching in the lateral dimension. The graft material exhibits similar viscoelastic properties in the longitudinal and lateral dimensions.

In one embodiment the submucosal tissue is stretched using 50% of the predicted ultimate load. The "ultimate load" is the maximum load that can be applied to the submucosal tissue without resulting in failure of the tissue (i.e. the break point of the tissue). Ultimate load can be predicted for a given strip of submucosal tissue based on the source and thickness of the material. Accordingly, one method of "conditioning" the tissue by stretching involves application of 50% of the predicted ultimate load to the submucosa for three to ten cycles. Each cycle consists of applying a load to the graft material for five seconds, followed by a ten second relaxation phase. The resulting conditioned submucosal tissue has a strain of less than 30%, more typically a strain from about 20% to about 28%. In one preferred embodiment conditioned the submucosal tissue has a strain of no more than 20%. The term strain as used herein refers to the maximum amount of tissue elongation before failure of the tissue, when the tissue is stretched under an applied load. Strain is expressed as a percentage of the length of the tissue before loading.

The conditioned submucosal tissue can be packaged and stored to maintain the conditioned state of the tissue. In one embodiment in accordance with the present invention, the conditioned submucosa is part of an article of manufacture that comprises submucosa and a support, wherein the support maintains the submucosa in a conditioned state. The conditioned submucosa and support can be enclosed within a container and sterilized to maintain the sterility of the submucosa. Alternatively, the conditioned submucosa and the support can be sterilized before enclosing the material within the container, and optionally exposed to a second round of sterilization after sealing the container. In one embodiment the conditioned submucosa is intestinal submucosa, and more particularly, comprises the tunica submucosa delaminated from both the tunica muscularis and at least the luminal portions of the tunica mucosa.

Accordingly, a package for storing graft material ready for use in a surgical procedure comprises, sterile submucosal tissue of a warm-blooded vertebrate, a support, and a sealed container. In this embodiment, the submucosal tissue is conditioned by stretching the submucosal tissue from a first length to a second length that is longer than the first length, the support maintains the tissue at its stretched second length, and the sealed container encloses and maintains the sterility of the submucosal tissue and the support. In one embodiment the submucosal tissue is stretched/conditioned to have a strain of less than 30%, and in another embodiment the tissue is stretched/conditioned to have a strain of no more than 20%.

The submucosal tissue can be conditioned before it is wrapped onto a spool, block or frame or it can be conditioned while, or as, the tissue is wrapped onto the spool, block or frame. In one embodiment, the submucosal tissue is conditioned while it is wrapped onto the spool, block or frame by fixing the end of a strip/sheet of conditioned submucosal tissue onto the spool, block or frame and wrapping the submucosal tissue onto the spool, block or frame under tension. The second end of the submucosal tissue is then immobilized to maintain the preconditioned length of the wrapped submucosal tissue.

For example, intestinal submucosa that has been delaminated from the tunica muscularis and at least the luminal portions of the tunica mucosa can be fed between a series of paired rollers, the free end attached to a spool (or other rotatable object) and rolled onto the spool. In one embodiment at least two sets of the paired rollers rotate at different speeds relative to one another, to place tension on the tissue located between the two rollers. The intestinal submucosa is thus stretched to a length greater than the original length of the delaminated intestinal submucosa and is immediately wrapped onto the spool to maintain the stretched condition of the intestinal submucosa. By varying the relative speed of the paired rollers the intestinal submucosa can be wrapped onto the roller and have a preselected strain.

Alternatively the conditioned intestinal submucosa can be held on a rigid frame to maintain the submucosa in its conditioned state. In one embodiment, the frame has opposite sides that are held in fixed position relative to one another, and the opposite sides are each provided with immobilizing means for immobilizing said submucosal tissue. The immobilizing means can be selected from clamps, sutures, staples, pins, glues or other tissue immobilizing techniques known to those skilled in the art. Preferably the frame is adjustable to several locked positions that vary the distance between the opposite sides to allow for various lengths of submucosa to be held within the frame and under tension.

Intestinal submucosa exhibits similar viscoelastic properties in all directions, i.e. the material can be stretched in any dimension to reduce the strain of the material. The material does not immediately return to its original size; it remains in a "stretched" condition. Accordingly, the delaminated intestinal submucosa can be stretched in a first dimension along a first axis and then stretched in a second dimension along a second axis wherein the first and second axis are not parallel to one another. In one embodiment the delaminated submucosa is stretched in a first dimension along a first axis and then stretched in a second dimension along a second axis, wherein the first axis and second axis are perpendicular to one another, to produce a graft construct that has a width and length longer than the original delaminated tissue.

Typically the conditioned submucosal tissue is immobilized by clamping, suturing, stapling, gluing (or other tissue immobilizing techniques) the tissue to the support, wherein the tissue is held at its preconditioned length in at least one dimension. In one embodiment the delaminated intestinal submucosa is conditioned to have a width and length longer than the original delaminated tissue and the conditioned length and width of the tissue is maintained by immobilizing the submucosa on a support. The support-held conditioned submucosal tissue can be sterilized before or after being packaged.

Unitary large area sheets of submucosal tissue and multi-layered constructs, as described in U.S. application Ser. No. 08/418,515 and PCT application Ser. No. PCT/US96/04721 the disclosures of which are expressly incorporated herein by reference, can be utilized in accordance with the present invention to form graft constructs for heart tissue repair. These multi-laminate constructs are formed by overlapping individual strips of submucosal tissue and applying pressure to the overlapped portions to fuse the tissues together. In one embodiment pressure is applied to the overlapped tissue under conditions allowing dehydration of the submucosal tissue.

The present submucosal tissue constructs may be sterilized using conventional disinfection/sterilization techniques including tanning with glutaraldehyde, formaldehyde tanning at acidic pH, ethylene oxide treatment, propylene oxide treatment, gas plasma sterilization, gamma radiation or electron beam treatment, and peracetic acid disinfection. Sterilization techniques which do not significantly weaken the mechanical strength. and biotropic properties of the graft are preferred. For instance, strong gamma radiation may cause loss of strength of the sheets of submucosal tissue. Preferred sterilization techniques include exposing the graft to peracetic acid, 1–4 Mrads gamma irradiation (more preferably 1–2.5 Mrads of gamma irradiation) or gas plasma sterilization. Typically, the submucosal tissue is subjected to two or more sterilization processes. After the submucosal tissue is treated in an initial disinfection step, for example by treatment with peracetic acid, the tissue may be wrapped in a plastic or foil wrap and sterilized again using electron beam or gamma irradiation sterilization techniques.

EXAMPLES
Repair of Atrial Septal and Ventricular Defects

Intestinal submucosal tissue grafts were implanted in four dog hearts. Isoflurane anesthesia and cardiopulmonary bypass were used during the procedure. In two of the four dogs an atrial septal defect was made, about the size of a nickel, and the defect was patched with peracetic acid cleansed porcine intestinal submucosa delaminated from both the tunica muscularis and at least the luminal portions of the tunica mucosa. These dogs were designated MA1 and MA2.

In the remaining two dogs (MV1 and MV2), a hole the size of a quarter, was made in the right ventricle near the base, and then patched with small intestinal submucosal tissue delaminated from both the tunica muscularis and at least the luminal portions of the tunica mucosa. The submucosal tissue was implanted with the luminal side facing the blood. The luminal surface of the intestinal submucosal tissue is the surface facing the lumen of the organ source and typically adjacent to an inner mucosa layer in vivo whereas the abluminal surface is the submucosal surface facing away from the lumen of the organ and typically in contact with smooth muscle tissue in vivo. The luminal surface is smoother and generally has more thrombo resistance than the abluminal surface.

Approximately eleven weeks after implantation, MA1 and MV2 were barbiturate-anesthetized, positive-pressure ventilated and the chests were opened. The hearts were then photographed in situ. The location of the submucosal tissue graft patch on the right ventricle of MV2 was visible as a suture ring about one half of the diameter of the size when the patch was made originally. The pericardium was adherent to the graft site. The ventricles were fibrillated electrically and a 1×1 cm specimen was removed from the center of the graft area. A 1×1 cm specimen was also excised from adjacent ventricular native myocardium and compared to the remodeled graft. The remodeled graft tissue was found to be slightly thinner than adjacent native ventricular myocardium.

The excised specimen of the remodeled MV2 graft was tested for its ability to contract using the following technique. Sutures were applied to the four corners of the graft. With this arrangement the contractile force could be measured along three axes. The remodeled graft tissue was mounted in an oxygenated tissue bath containing Krebs solution maintained at 37° C. and connected to a myograph.

Figure 2:
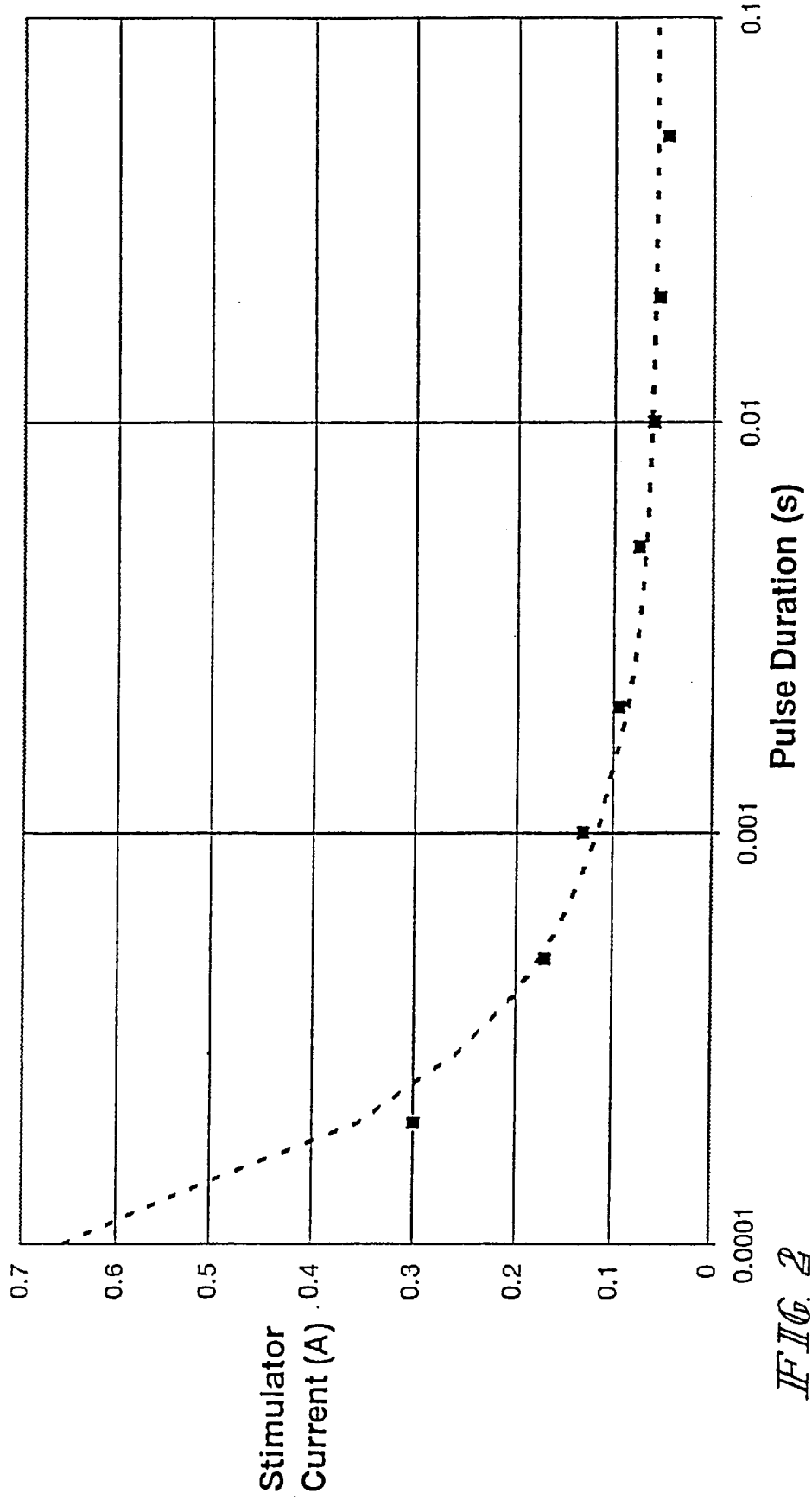
FIG. 2 is a graphic representation of strength-duration data for remodeled canine ventricular myocardium of the MV2 dog (Rheobase=55.42 mA).

The MV2 specimen remodeled graft tissue exhibited spontaneous contractions and relaxations at an irregular slow-rate, as shown in FIG. 1 (1,2,3). In addition the tissue was tested to determine if the tissue was responsive to electrical stimuli. A single stimulus was delivered to plate electrodes in the tissue bath. These electrodes were not in contact with the specimen, and thus the stimulating current was carried by the tissue-bath fluid. The remodeled graft tissue (MV2) contracted in response to a single stimulus, as shown in FIG. 1 (50 ms, 160 mA). A strength-duration curve was obtained, i.e. a plot of the strength of a threshold stimulus needed to evoke a contraction versus stimulus duration. FIG. 2 shows the strength-duration curve for the remodeled graft tissue of MV2, exhibiting a chronaxie of 1.08 ms; the chronaxie for normal myocardium is typically 1.4 ms. A strength-duration curve was not obtained for the adjacent native myocardium.

As noted above, the MA1 dog, implanted with the atrial septal graft, was barbiturate-anesthetized, positive-pressure ventilated, the chest opened and the heart was photographed. The ventricles were fibrillated electrically and the heart was removed. The atrial septal graft was removed and examined. The atrial septal graft was firmer than the surrounding myocardium and slightly more pale. No blood clots (thrombi) were found in the right ventricle or in either atrium.

Figure 3:
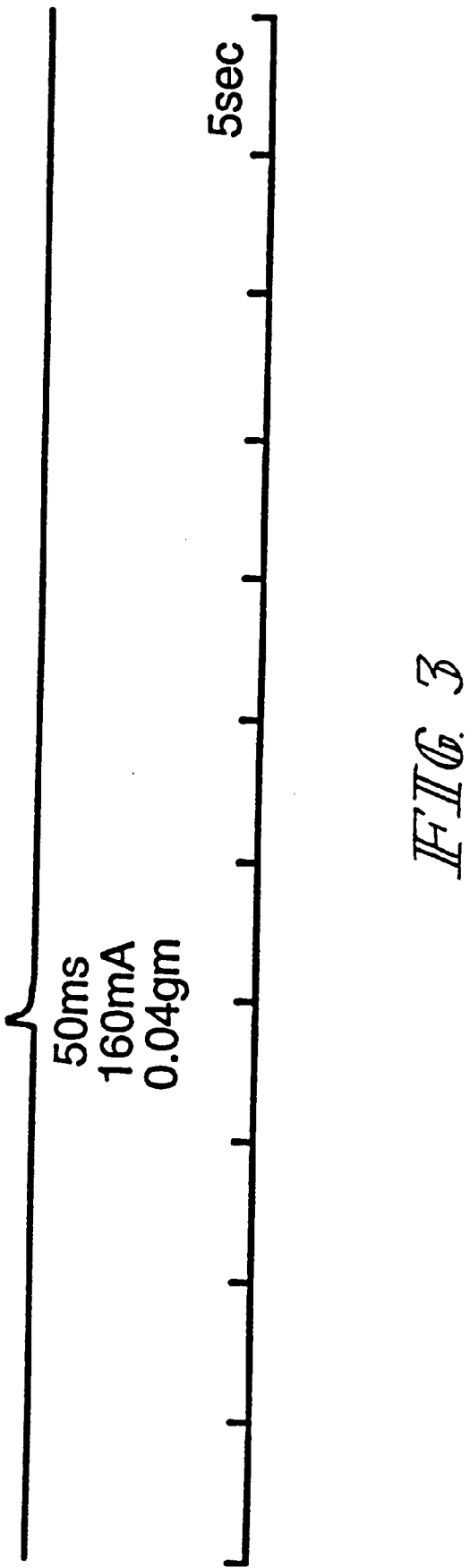
FIG. 3 illustrates myographic data for remodeled canine atrial septum in the MA1 dog when the tissue was exposed to electrical stimulation (50 ms, 160 mA).

Sutures were placed in the corners of the remodeled atrial septal graft. When mounted in the tissue bath, no spontaneous contractions were evident. Response to single electrical stimuli was recorded as shown in FIG. 3. It is not surprising that the contraction was weak because septal tissue is not known to be contractile.

Table 1 summarizes the dates when the implants were made and when those specimens were explanted.

TABLE 1

IMPLANT & EXPLANT DATES

| ANIMAL | IMPLANT | EXPLANT | DAYS |
|---|---|---|---|
| MA1 | 1/22/96 | 4/9/96 | 78 |
| MA2 | 1/23/96 | 6/18/96 | 148 |
| MV1 | 1/24/96 | 6/18/96 | 147 |
| MV2 | 1/24/96 | 4/9/96 | 78 |

Histological Examination of Excised Tissues

Histologic examination of the remodeled right ventricular free wall graft (MV2) showed bundles of cardiomyocytes surrounded by organized collagenous connective tissue. The cardiomyocytes were morphologically normal with observable striations, centrally located nuclei, and a syncytial arrangement. Approximately 50% of the remodelled tissue was myocardial cells and the remaining 50% was collagenous connective tissue. The boundary between the graft and the normal ventricular wall was barely apparent (confirmed by suture placement) and there was bridging of this anastomotic site by the cardiomyocytes. Mason's trichrome stain confirmed the presence of these cardiomyocytes with an eosinophilic staining spindle cell containing striations and central nuclei. The tissue was highly vascularized. There was a normal endocardial lining.

Histologic examination of the remodeled interatrial septum graft showed a mixture of connective tissues including cardiomyocytes surrounded by a fibrous (collagenous) connective tissue and islands of cartilage, and small clusters of adipocytes. The cardiomyocytes were morphologically normal but occupied a small (perhaps 10 to 15%) of the total area. The fibrous connective tissue occupied the majority of the area which was examined. Cartilage appeared to represent approximately 20% of the area which was examined. The blood contacting surfaces of the interatrial graft site showed morphologically normal endocardium.

As shown in Table 1, MA2 survived for 148 days and MV1 for 147 days before sacrifice. MV1 experienced no complications during the study. However, MA2 developed atrial fibrillation during the 17 weeks after implantation.

Histologic examination of the remodeled atrial septal defect graft tissue of MA2 showed a mixture of connective tissue types within the tissue which once consisted of submucosal tissue. The mixture of tissues included myocardial tissue, well differentiated cartilage, fibrous connective tissue, and adipose connective tissue. The atrial lining consisted of endothelial cells. There was no evidence for an inflammatory reaction.

Histopathologic examination of the tissues taken from the right ventricular free wall graft site of MV1 showed the endocardial surface contained an intact endothelial layer with a deep accumulation of bundles of developing and well differentiated myocardial cells. These bundles of cells were of variable size and orientation and were associated with a small amount of fibrous connective tissue. The epicardial connective tissue replacement consisted of a thick bank of dense fibrous connective tissue. All tissues were highly vascularized. There was no evidence of any inflammatory cells in any of the tissues or sections examined. The myocardial tissue comprised approximately 65% of the graft area in the dog which survived 147 days.

Physiological Studies MA2 and MV1.

Figure 4:
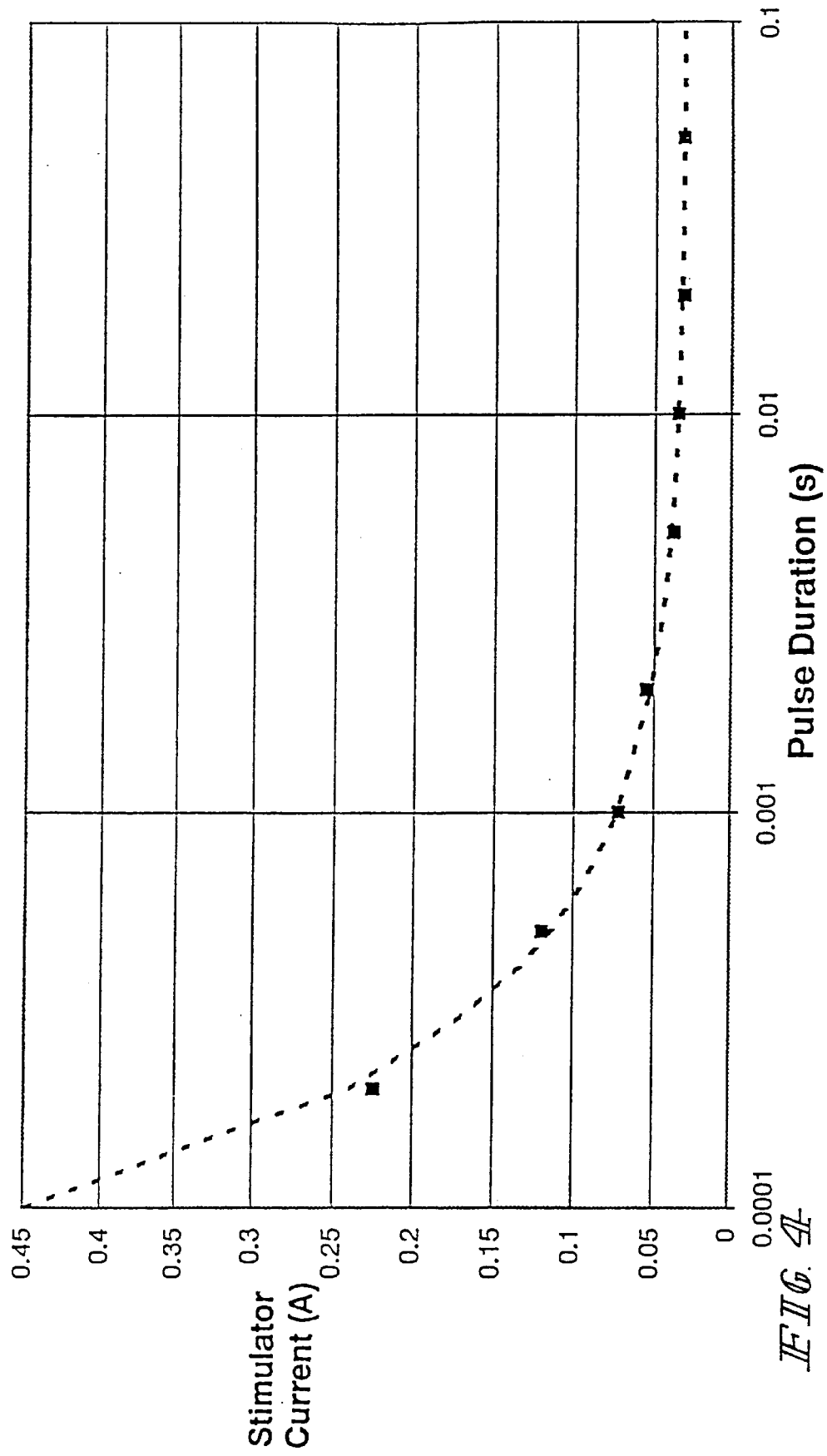
FIG. 4 is a graphic representation of strength-duration data for remodeled canine atrial septal tissues of the MA2 dog (Rheobase=30.9 mA).
Figure 5:
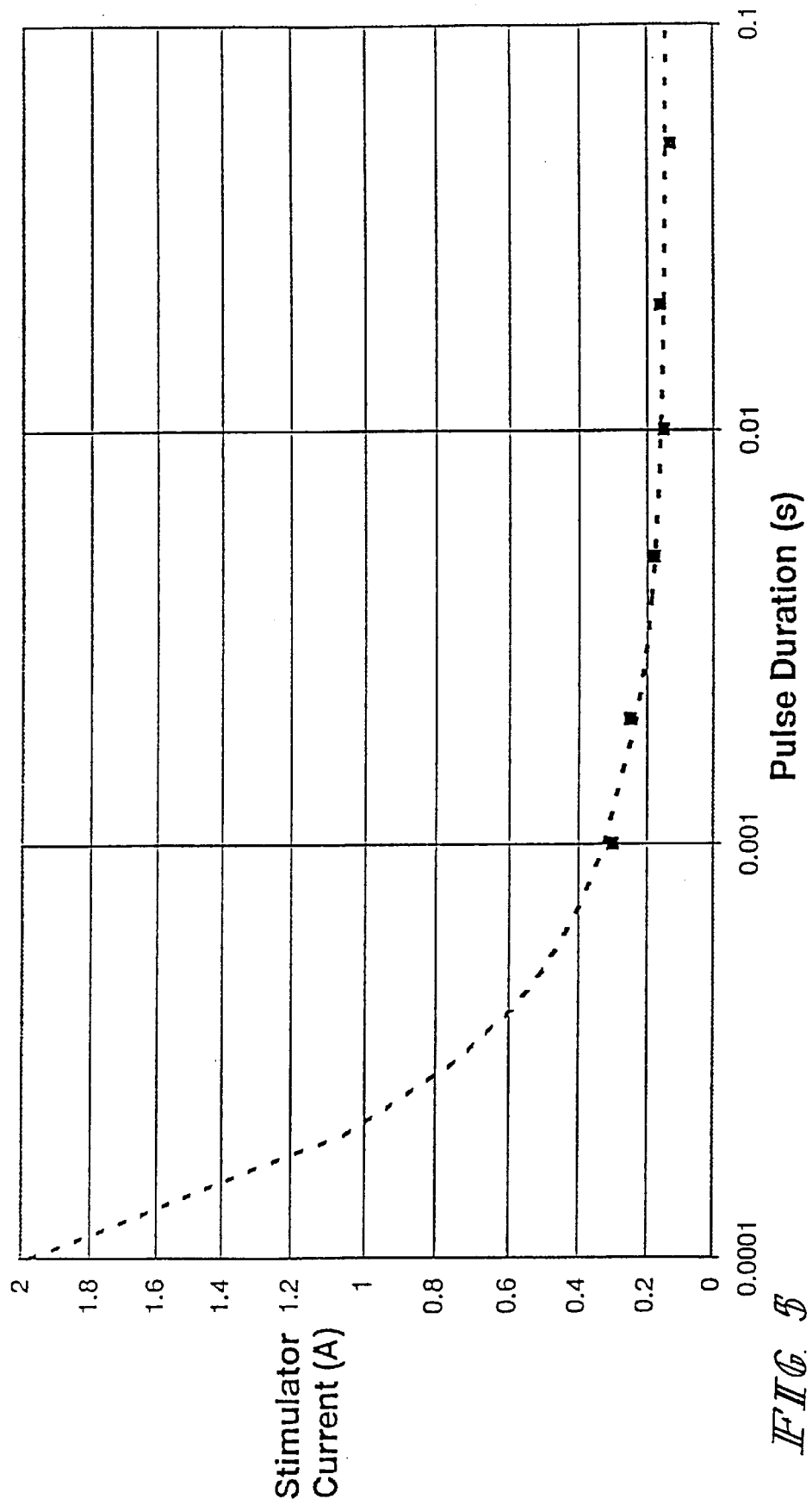
FIG. 5 is a graphic representation of strength-duration data for remodeled canine ventricular myocardium of the MV1 dog (Rheobase=139 mA).
Figure 6:
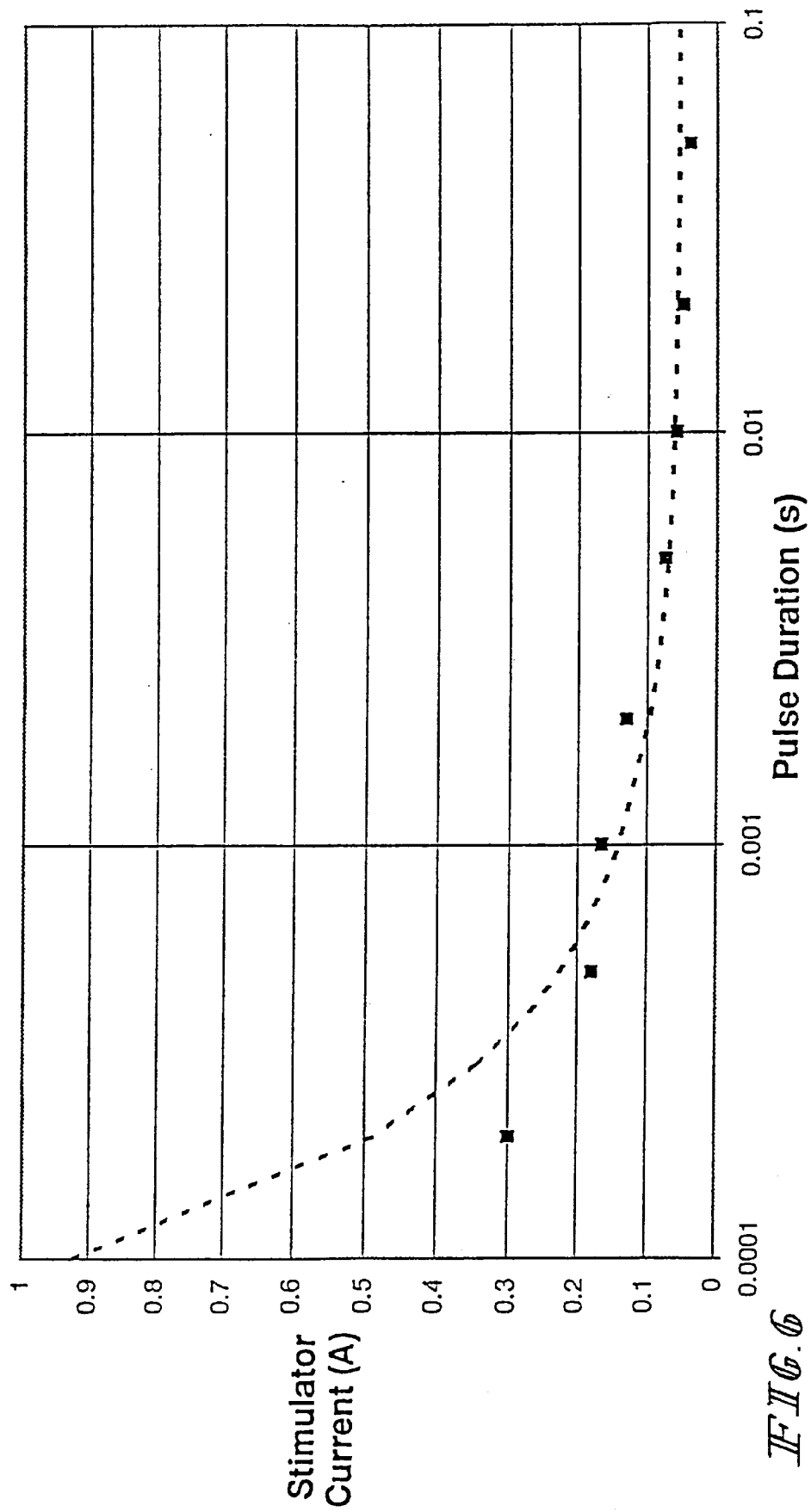
FIG. 6 is graphic representation of strength-duration data for normal canine ventricular tissue of the MV1 dog (Rheobase=55.42 mA).

The remodeled atrial and ventricular grafts were placed in the tissue bath and connected to a myograph. No spontaneous contractions and relaxations were observed in either the remodeled atrial or ventricular grafts. However, both were responsive to electrical stimulation and strength-duration curves were obtained, as shown in FIG. 4 (MA2) and FIG. 5 (MV1). A strength-duration curve was obtained for normal MV1 canine ventricle (FIG. 6). Table 2 summarizes the chronaxie values for all 4 dogs.

TABLE 2

CHRONAXIE VALUES

| ANIMAL NUMBER | CHRONAXIE REMODELED | (MSEC) NATIVE |
|---|---|---|
| MA1 | — | — |
| MA2 | 1.35 | — |
| MV1 | 1.32 | 1.63 |
| MV2 | 1.08 | — |

What is claimed is:

1. A method for promoting endogenous regrowth and healing of damaged or diseased cardiac tissues, said method comprising contacting said damaged or diseased tissues with a composition comprising submucosal tissue of a warm blooded vertebrate.

2. The method of claim 1 wherein the step of contacting the damaged or diseased cardiac tissues comprises surgically implanting a patch of submucosal tissue at the site in need of repair.

3. The method of claim 2 wherein the submucosal tissue is conditioned so that the tissue has a strain of less than 30%.

4. The method of claim 2 wherein the submucosal tissue is conditioned so that the tissue has a strain of no more than 20%.

5. The method of claim 1 wherein the submucosal tissue is fluidized and the fluidized tissue is injected into or adjacent to said damaged or diseased cardiac tissues.

6. The, method of claim 2 wherein the submucosal tissue is implanted into the atrial and ventricular myocardium to remodel into myocadial tissue that functions as an A-V bridge for conducting excitation from the S-A node to the ventricles.

7. An article of manufacture comprising intestinal submucosa and a support wherein the intestinal submucosa is conditioned to have a strain of less than 30% and the support holds and maintains the tissue in its conditioned state.

8. The article of manufacture of claim 7 wherein the intestinal submucosa and the support are sterilized.

9. The article of manufacture of claim 8 further comprising a sealed container that encloses and maintains the sterility of said intestinal submucosa and said support.

10. The article of manufacture of claim 7 wherein the intestinal submucosa comprises the tunica submucosa delaminated from both the tunica muscularis and at least the luminal portions of the tunica mucosa.

11. The article of manufacture of claim 7 wherein the support is a spool and the intestinal submucosa is wrapped onto the spool under sufficient tension to maintain the intestinal submucosa in its conditioned state.

12. The article of manufacture of claim 7 wherein the support is a frame having opposite sides for holding said intestinal submucosa, wherein said opposite sides are held in fixed position relative to one another.

13. The article of manufacture of claim 12 wherein at least one of the opposite sides further comprises a clamp.

14. The article of manufacture of claim 9 wherein the intestinal submucosa comprises the tunica submucosa delaminated from both the tunica muscularis and at least the luminal portions of the tunica mucosa.

15. The article of manufacture of claim 9 wherein the support is a spool and the intestinal submucosa is wrapped onto the spool under sufficient tension to maintain the intestinal submucosa in its conditioned state.

16. The article of manufacture of claim 9 wherein the support is a frame having opposite sides for holding said intestinal submucosa, wherein said opposite sides are held in fixed position relative to one another.

17. The method of claim 1 wherein the submucosal tissue comprises intestinal submucosa delaminated from both the tunica muscularis and at least the luminal portion of the tunics mucosa.

18. An article of manufacture comprising submucosal tissue of a warm blooded vertebrate and a support wherein the submucosal tissue is conditioned to have a strain of less than 30% and the support holds the tissue in its conditioned state.

19. The article of manufacture of claim 18 wherein the submucosal tissue and the support are sterilized.

20. The article of manufacture of claim 19 further comprising a sealed container that encloses and maintains the sterility of said submucosal tissue and said support.

21. The article of manufacture of claim 18 wherein the submucosal tissue comprises the tunica submucosa delaminated from both the tunica muscularis and at least the luminal portion of the tunica mucosa.

22. The article of manufacture of claim 18 wherein the support is a spool and the submucosal tissue is wrapped onto the spool under sufficient tension to maintain the submucosal tissue in its conditioned state.

23. The article of manufacture of claim 18 wherein the support is a frame having opposite sides for holding said submucosal tissue, wherein said opposite sides are held in a spaced-apart relationship.

24. The article of manufacture of claim 23 wherein at least one of the opposite sides further comprises a clamp.

25. The article of manufacture of claim 20 wherein the submucosal tissue comprises the tunica submucosa delaminated from both the tunica muscularis and at least the luminal portions of the tunica mucosa.

26. The article of manufacture of claim 20 wherein the support is a spool and the submucosal tissue is wrapped onto the spool under sufficient tension to maintain the submucosal tissue in its conditioned state.

27. The article of manufacture of claim 20 wherein the support is a frame having opposite sides for holding said submucosal tissue, wherein said opposite sides are held in a spaced-apart relationship.

* * * * *